(12) United States Patent
Assmann et al.

(10) Patent No.: US 9,008,750 B2
(45) Date of Patent: Apr. 14, 2015

(54) METHOD FOR DETERMINING THE VENTILATION OF A LUNG

(75) Inventors: Stefan Assmann, Erlangen (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 617 days.

(21) Appl. No.: 12/820,356

(22) Filed: Jun. 22, 2010

(65) Prior Publication Data

US 2010/0324409 A1 Dec. 23, 2010

(30) Foreign Application Priority Data

Jun. 22, 2009 (DE) .......................... 10 2009 030 110

(51) Int. Cl.
*A61B 5/05* (2006.01)
*A61B 5/055* (2006.01)
*A61B 5/08* (2006.01)
*A61B 5/00* (2006.01)

(52) U.S. Cl.
CPC . *A61B 5/055* (2013.01); *A61B 5/08* (2013.01); *A61B 5/721* (2013.01)

(58) Field of Classification Search
None
See application file for complete search history.

(56) References Cited

U.S. PATENT DOCUMENTS

| 2003/0055331 A1* | 3/2003 | Kotmel et al. | 600/410 |
| 2006/0264736 A1* | 11/2006 | Ehman et al. | 600/410 |
| 2007/0225592 A1* | 9/2007 | Ruppert et al. | 600/420 |
| 2009/0048505 A1* | 2/2009 | Kuth et al. | 600/410 |

FOREIGN PATENT DOCUMENTS

| DE | 103 18 429 A1 | 11/2004 |
| DE | 10 2005 010 093 A1 | 9/2006 |

* cited by examiner

*Primary Examiner* — Nicholas Evoy
(74) *Attorney, Agent, or Firm* — Schiff Hardin LLP

(57) ABSTRACT

In a method for determining the ventilation of a lung of an object under examination by magnetic resonance imaging, at least two first lung-representing image data sets are acquired at different intervals of the breathing phase. The density change of the lung tissue is automatically determined from the signal difference between the image signals of the first image data sets in at least one corresponding region of the first lung-representing image data set. The lung or the thorax volume is automatically determined using at least two of the first image data sets, or using at least an additional second lung-representing image data set in a breathing phase that corresponds with the breathing phase of a first image data set. The localized, quantitative ventilation of the lung is automatically calculated depending on the density change of the lung tissue and the change of the lung or thorax volume.

15 Claims, 4 Drawing Sheets

METHOD FOR DETERMINING THE VENTILATION OF A LUNG

BACKGROUND OF THE INVENTION

1. Field of the Invention

The present invention involves a method for determining the ventilation of a lung of an object under examination by means of magnetic resonance imaging.

2. Description of the Prior Art

The process of imaging the lung by means of magnetic resonance imaging basically confronts the user with two problems. The torso of the subject keeps moving because of breathing, with one breathing cycle being about 5 seconds long. Moreover, in addition to the blood vessels, the lungs are basically composed of pulmonary alveoli, and the tissue of an alveolus encloses an air-filled space. This tissue has therein protons and, accordingly can be detected in a magnetic resonance measurement. However, the various air-tissue transitions result in susceptibility jumps (discontinuities) that can cause signal losses. This is especially the case with gradient-echo based methods starting at a field strength of about 1.5 tesla. In order to avoid such artifacts, it is possible to use spin-echo based methods, or the gradient-echo based methods have to be implemented with a minimal echo time.

If several lung-representing image data sets are acquired during one breathing cycle, it is possible by comparing the signal intensities to determine the relative change in ventilation of a specific lung region. This relative change in ventilation is available in the form of a factor by which the ventilation of the image with the lower signal intensity of the lung tissue has been increased in comparison to the image data with a higher signal intensity of the lung tissue. This is the case because by filling the alveoli with air, the tissue portion in an observed volume element is decreased, which reduces in the respective image region the signal intensity with increasing ventilation.

Since only the relative change in ventilation is known, it is difficult to compare the values of different patients.

Spirometry is another known method for determining ventilation parameters. To this end, a spirometer is used to record the change in the lung volume as well as the time course of the change. However, a spirometer can determine only the changes in relation to the lung as a whole.

SUMMARY OF THE INVENTION

An object of the invention is to provide a method of the type mentioned above by means of which the ventilation of the lung tissue can be determined on a quantitative and localized basis.

This object is achieved in accordance with the invention by a method that includes the following steps.

At least two first lung-representing image data sets are acquired at different intervals of the breathing phase.

The density change of the lung tissue is determined by determining the signal difference from the image signals of the first image data sets in at least one corresponding region of the first lung-representing image data set.

The lung or the thorax volume is determined using at least two of the first image data sets, or using at least an additional second lung-representing image data set in a breathing phase that corresponds with the breathing phase of a first image data set.

The localized, quantitative ventilation of the lung is calculated depending on the density change of the lung tissue and the change of the lung or thorax volume.

The inventive method is based on recording not only the density change of the lung tissue but also at the same time recording the volume change of the lung. Based on the relative change in ventilation, it can be transferred into quantitative ventilation through multiplication with a correction value. This factor results from dividing the volume change of the lung with the signal change or signal difference of the lung as a whole. Since the relative ventilation is available of a localized basis, the quantitative ventilation is also localized.

In accordance with the invention, it is essential to simultaneously record the density or density change of the lung tissue and the lung volume. It is therefore preferred that at least one of the first image data sets is acquired in three spatial dimensions. The imaging method selected should be a method in which the lung tissue supplies image signals, which means that the signal is not eliminated because of susceptibility artifacts. Corresponding spin-echo based methods are, for example, spin-echo imaging, RARE or HASTE. These methods can be used with all field strengths. It is also possible to use gradient-echo based methods, such as FLASH, if these methods are used with minimized echo time. Furthermore, it is possible to use ultrafast methods, such as TrueFisp, provided the susceptibility artifacts and corresponding signal losses are not too strong. Generally the susceptibility artifacts increase with increasing magnetic field strength.

However, acquiring image data sets with three spatial dimensions is time consuming. Even with extremely fast methods, it is possible even with low resolution to acquire a three-dimensional image data set only within a period of a few seconds. To avoid that the volume of the lungs or the density of the lung tissue changes during the period of taking the three-dimensional image, the person has to hold his/her breath.

However, it is preferable to observe a person while he/she is breathing freely. To achieve this, at least one of the first image data sets can be acquired with two spatial dimensions. Alternatively, at least two of the first image data sets can be acquired with two spatial dimensions and in multislice operation. Depending on the resolution selected, two-dimensional image data sets can be taken faster than three-dimensional image data sets. However, in order to obtain certain three-dimensional information, it is possible to acquire several successive two-dimensional image data sets, with the layers aligned in parallel fashion to each other. Accordingly, this method is also called multislice operation.

Ideally, two as well as three-dimensional image data sets are acquired in the process of this method. By acquiring a three-dimensional first image data set with maximum inhalation and exhalation, respectively, it is possible to determine accurate volume envelopes of the lung or the thorax. The three-dimensional image data sets have to be acquired when the person holds his/her breath. The two-dimensional image data sets, on the other hand, can be acquired while the person is breathing freely. With the use of an imaging method such as FLASH, a two-dimensional image can be acquired during a period of only 200 ms. Of course, this time estimate depends on the selected resolution. Accordingly, during a breathing cycle of 5 seconds, it is possible to acquire 25 image data sets per breathing cycle. The volume associated with a two-dimensional first image data set can be determined in that a three-dimensional model of the enveloping surface of the lung is determined from the three-dimensional first image data sets and that the envelope curve of the lung is determined from the two-dimensional first image data sets. In the next step, the three-dimensional model is deformed in such a way that it matches the measured two-dimensional envelope curves, from which the volume as a whole is determined.

However, it is also possible to record the volume of the lung and its change with at least a second image data set. Second image data sets differ from first image data sets in that they do not comprise a signal in the lung region. This is the case, for example, with gradient-echo based methods in which the echo time has not been minimized. It applies also to the TrueFisp method with field strengths starting at app. 1.5 tesla. However, the advantage of these methods is their speed. For a determination of the lung or thorax volume at least a second lung-representing image data set with three spatial dimensions can be acquired. Consequently, it is possible especially with ultrafast imaging methods to take a repeated image of the lung as a whole. At the same time, it is possible to minimize the time required for a person to hold his/her breath. From the image data set thus acquired it is also possible to prepare a 3D model of the enveloping surface of the lung. In order to further accelerate the determination of the lung or thorax volume, at least a second lung-representing image data set with two spatial dimensions can be acquired. As described above, this method will accelerate data recording because it keeps the volume of the data to be acquired at a minimum. As a special advantage, it is possible to acquire at least a pair of two second lung-representing image data sets which are basically arranged in orthogonal fashion to each other. It is also possible to acquire three second image data sets which are basically arranged in orthogonal fashion to each other. From the two-dimensional second image data set or the two-dimensional second image date sets, envelope curves can be obtained to which the 3D model of the enveloping surface of the lung is adapted.

In the process, the lung or thorax volume can be automatically segmented by using a threshold value of the signal intensity of the image signals of the second image data set. Since the second image data sets in the lung region do not comprise a signal it is relatively easy to perform an automatic segmentation of the lung or thorax volume.

Instead of acquiring additional second image data sets, at least one additional navigator echo can be acquired for at least two of the first image data sets in order to determine the lung or thorax volume. Acquiring a navigator echo is actually a technologically well-known process by means of which it is possible to track the position of specific objects. Preferably, the lung or thorax volume can be determined by means of elasticity values in which each lung-defining tissue is assigned its own elasticity value and a navigator echo tracks a respective point of a specific tissue. In this way it is possible to take into account the fact that the different tissue surrounding the lung shows different degrees of movement of deformation. In acquiring two-dimensional first image data sets, the acquisition of navigator echoes is especially suitable for recording the change of the volume envelope of the lung in the dimension that is not displayed in the two-dimensional first image data set.

It is of special advantage that at least a first image data set is acquired with maximum inspiration and at least one first image data set with maximum expiration. Maximum inspiration, i.e., inhalation, results in maximum lung volume and minimum tissue density. Maximum expiration, i.e., exhalation, results in exactly the opposite. In this way it is possible to obtain the best possible accuracy in the respective difference calculation, or the calculation of the change in tissue density or lung volume.

Advantageously, the breathing phase of the object under examination can be recorded with a respiratory sensor in order to record the inspiration or expiration. It is of special advantage if the respiratory sensor used is a spirometer. By means of said spirometer, it is possible to determine the lung volume as well as its change in the curse of the breathing cycle.

Advantageously, the signal difference can be determined pixel by pixel. Accordingly, the density changes of the tissue, which form a basis for measuring the signal difference, are also available pixel by pixel. This, in turn, results in a quantitative pixel by pixel perfusion. However, if there is minor signal intensity in the individual pixels it is also possible to use an average of two or several pixels in order to decrease the variance of the ventilation value.

However, the density change of the lung tissue and the supplied air volume are not necessarily linear. It is therefore possible to determine the ventilation by means of a calibration curve which describes the connection between the density change of the lung tissue and the supplied air volume. This calibration curve is determined in phantom trials.

DESCRIPTION OF THE PREFERRED EMBODIMENTS

Figure 1:
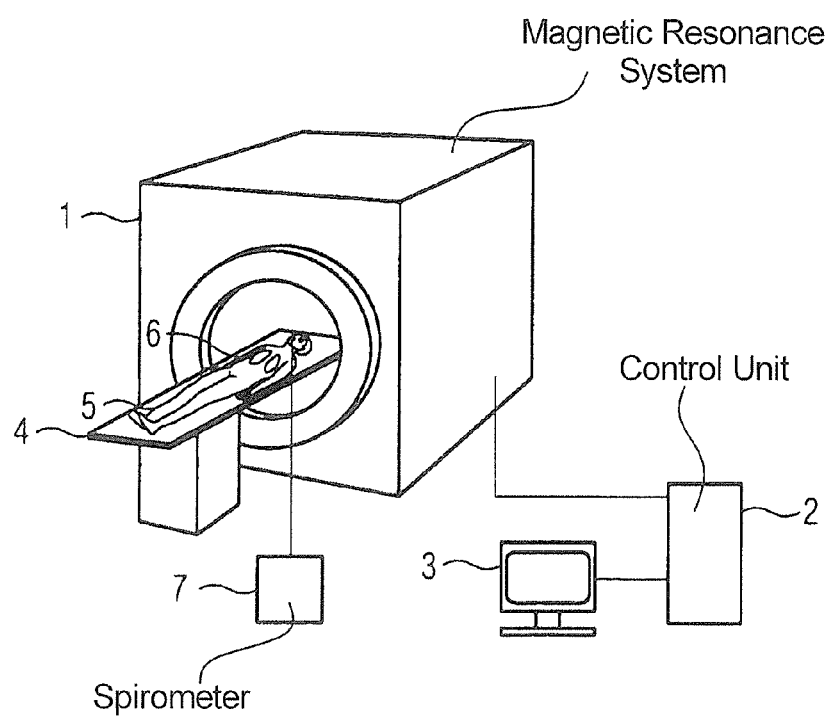
FIG. 1 schematically illustrates a magnetic resonance system.

FIG. 1 shows a magnetic resonance system 1 having a control unit 2 and a monitor 3. Furthermore, the magnetic resonance system 1 has a patient bed 4 on which the person 5 is moved through the opening of the magnetic resonance system 1. The person 5 is positioned on the patient bed 4 in such a way that his/her lung 6 can be positioned in the iso-center of the magnetic resonance system 1. In addition to the magnetic resonance system 1, a spirometer 7, is available in order to record the ventilation parameters of the person 5.

Figure 2:
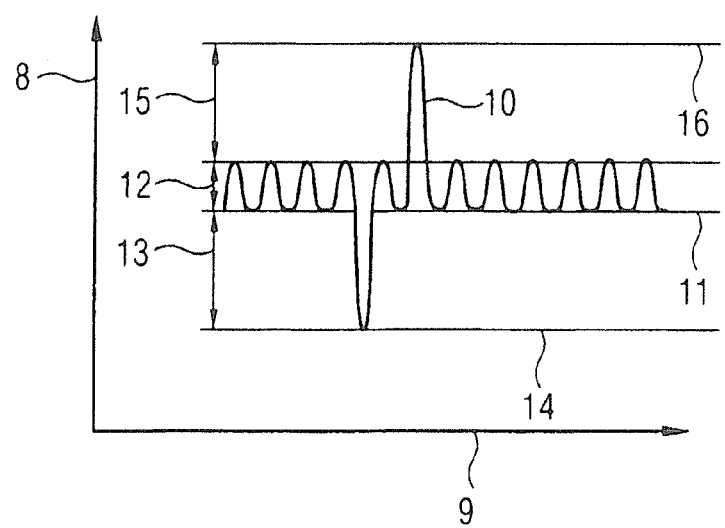
FIG. 2 illustrates a spirogram.

To illustrate the relevant parameters, FIG. 2 shows a respective spirogram. The lung volume is applied along the axis 8, while the axis 9 displays the time. The curve shows the lung volume of the person 5 over several breathing cycles. Starting from the resting end-expiratory position 11, the lung volume increases and decreases by the tidal volume 12. However, the person can also exhale beyond the resting end-expiratory position 11, namely by the expiratory reserve volume 13. In the process, the lung volume can be decreased up to the maximum expiration position 14. However, it is also possible to increase the lung volume by the inspiratory reserve volume 15 up to the maximum inspiration position 16. At the same time, the lung volume does not equal zero even in the maximum expiration position 14, but a residual volume remains in the lung even with maximum exhalation.

Figure 3:
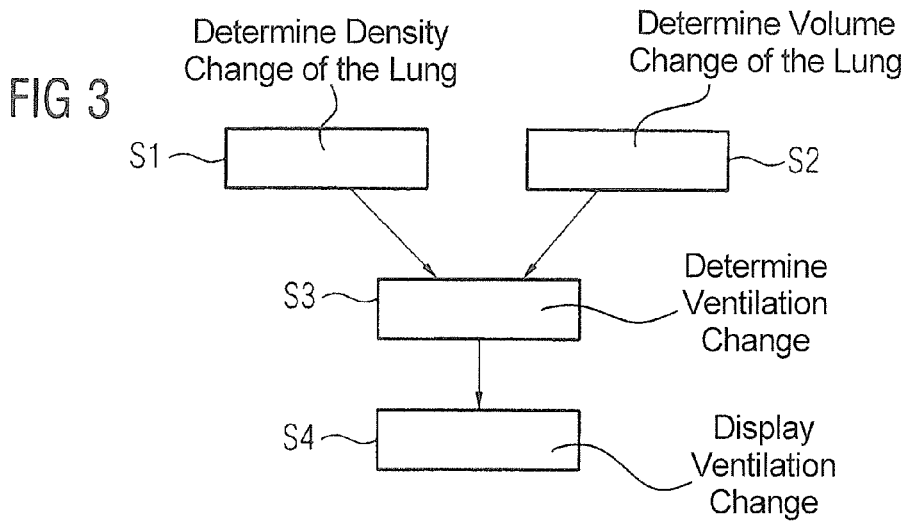
FIG. 3 is a flow chart of an embodiment of the inventive-based method.

FIG. 3 shows a flow chart for determining the ventilation parameters of a lung by means of a magnetic resonance system. In a first step S1, the density change of the lung is determined. This requires at least two lung-representing image data sets. If S1 depicts the average signal intensity of a lung-representing image region of the first image, in which the image region can be a single pixel or a large number of pixels, and S2 depicts the signal intensity of a corresponding region in a condition of inhalation, this will result in the relative ventilation of $$V_{rel} = \frac{S_1 - S_2}{S_1 - S_R} \quad (1)$$

$S_R$ depicts the signal of the background noise.

Basically, any point in time of the breathing phase can be used as starting point for calculating the relative ventilation. The respective calculated change refers always to the starting point. This starting point does not have to meet specific requirements. However, it is preferable to use a data set which represents the lung at the point of maximum inspiration or maximum expiration because, based on this, positive or negative ventilation changes always imply the breathing phase.

Moreover, in step S2 the volume change of the lung is determined. The further description provides a more detailed explanation of the succession of image recording of the image data sets for determining the density change and the volume change.

From the parameters determined in steps S1 and S2, the relative ventilation change can be transferred (transformed) into an absolute and quantitative ventilation change in Step S3. For this purpose, the change of the signal intensity in the entire region representing the lung has to be determined:

$$\Delta S = \sum_i s_{1i} - \sum_i s_{2i} \quad (2)$$

A pixel or voxel of the image of the lung in a condition of exhalation is therefore depicted with $s_{1i}$ and the precisely corresponding image region in a condition of inhalation is depicted with $s_{2i}$. Since the density change of the tissue is exactly proportional to the signal change, $\Delta S$ depicts also the density change of the tissue.

The volume change can be easily determined by subtracting the volume of the lung in a condition of exhalation $V_1$ from the volume of the lung in a condition of inhalation $V_2$:

$$\Delta V = V_2 - V_1 \quad (3)$$

The absolute ventilation change results from the previously mentioned parameters according to the equation (4):

$$V_{abs} = V_{rel} \cdot \frac{\Delta V}{\Delta S} \quad (4)$$

Finally, the localized and quantitative ventilation change thus determined can be displayed as step S4 on a display system, such as the monitor 6.

The parameters used can be illustrated by means of a numeric example. In the example, the lung in a condition of inspiration comprises 1,000 voxels, measuring 8 cm$^3$ each, in which the lung volume has increased by 2 liters during the inspiration process. This results in an average ventilation change $V_{rel}$ of 0.3 cm$^{-3}$. This value results from an averaging of all 1,000 voxels. Accordingly, the entire change in ventilation amounts to 0.3×1,000, which corresponds to 300 units. The volume change of 2 liters is associated with this signal or density change. 2 liters correspond to 2,000 cm$^3$; the corresponding conversion factor is 6.66.

Several possibilities are available for determining the density change of the lung tissue and the volume according to steps S1 and S2 of the lung. These steps are subsequently explained in more detail.

Figure 4:
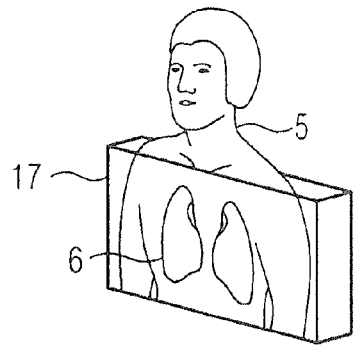
FIG. 4 shows the arrangement of a three-dimensional image data set.

FIG. 4 shows a 3D image data set 17 representing the chest region of the person 5. In the lung region 6 this image data set can comprise signals. This case involves a first image data set. If it does not comprise a signal in the lung region, it involves a second image data set. This definition also applies to all image data sets subsequently described.

Figure 5:
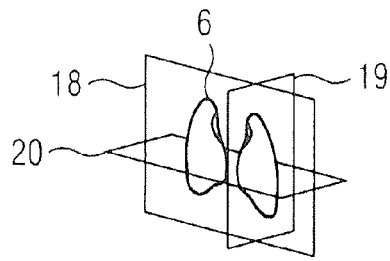
FIG. 5 shows the arrangement of two-dimensional image data sets with respect to a subject.

FIG. 5 shows the possible positions of two-dimensional image data sets. The image data set 18 with a coronal position is the preferred recording position, because it represents the greatest possible surface of the lung. However, it is also possible to record image data sets 19 with a sagittal position and image data sets 20 with an axial position. In addition, one or several navigator echoes can be recorded for each of the image data sets 17 to 20 described.

Figure 6:
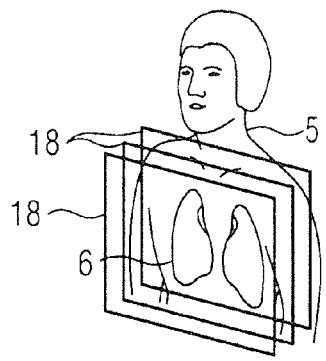
FIG. 6 shows the arrangement of parallel two-dimensional image data sets with respect to a subject.

FIG. 6 shows an arrangement for recording several image data sets 18 in multislice operation with a coronal position. These image data sets 18 with a coronal position represent the same spatial region of the person 5. However, with regard to layer positioning they are shifted parallel. Ideally, the image data sets 18 with a coronal position are arranged in such a way that no empty spaces are formed between the layers.

From these possibilities for data collection, the most different successions of image recording can be generated.

Figure 7:
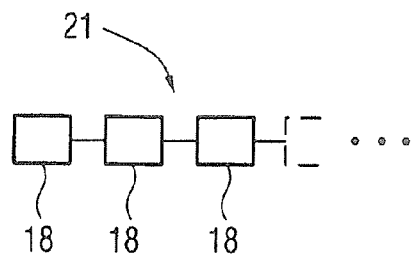
FIG. 7 shows a first embodiment of successive image recordings.

FIG. 7 shows a first possibility of succession of image recording 21. In the process, image data sets 18 with coronal position are recorded in immediate succession. Naturally, these involve first image data sets. Consequently, the image data sets 18 show a signal intensity in the lung region, which exceeds the noise and which is proportional to the density of the lung tissue. As previously shown in the equation (2), it is very easy to determine the change in density of the lung tissue. In order to be able to calculate the lung volume merely from the coronal image data sets 18, it is required to prepare beforehand a statistical model by measuring the lung of a person. By means of these statistical data, it is possible to calculate the respective volume of the lung from an envelope curve of the lung determined from an image data set 18 with a coronal position. Obviously, the statistical model of the lung must comprise volume envelope of different times of the breathing phase. Alternatively, it is also possible to select from the series of image data sets 18 with a coronal position the image data sets which were recorded during maximum expiration or maximum inspiration, either in rest position or in maximum expiration position, in order to determine the volume change of the lung. The volume change for the remaining image data sets is then calculated by means of a simple interpolation. This simple succession of image recording 21, which can only be performed with previous knowledge, can, of course, not be performed with people whose lung has experienced a volume change because of a disease. This does not apply to the case where even for this atypical case a statistical model could be prepared and has been prepared.

To the succession of image recording 21 and all successions of image recording subsequently described it certainly applies that in the figures only one or two occurrence patterns are shown, which can be repeated many times. As described above, up to 25, or even more, image data sets can be recorded in a breathing cycle and not, as described in the figures, only three or four. Covering a single breathing cycle requires that at least these 25 image data sets are recorded. As a general rule, the successions of image recording are repeated until a variety of breathing cycles has been covered. Ten breathing cycles will already result in approximately 250 image data sets; more breathing cycles will result in proportionally more image data sets.

Figure 8:
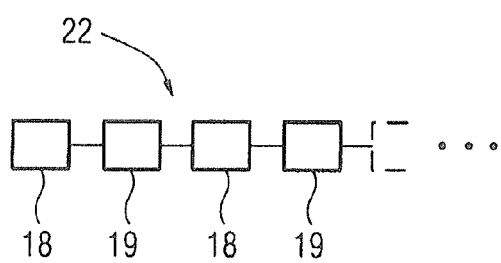
FIG. 8 shows a second embodiment of successive image recordings.

FIG. 8 shows the succession of image recording 22 that does not require a statistical model. In this image recording, image data sets 18 with coronal position and image data sets 19 with sagittal position are recorded alternately. The image data sets 18 are first image data sets, i.e., they show signals in the lung region. This applies also to the further embodiments. However, the image data sets 19 with sagittal position are not required for determining the density change of the lung tissue. It is therefore sufficient that they are designed as second image data sets, i.e., that they show only tissue outside the lung. However, this information is adequate for determining the lung or thorax volume. Arranging image data sets as second image data sets is always interesting with measuring systems which are very fast compared to other measuring systems, but which are not able to record a signal in the region of the lung tissue because of the characteristics of the measuring system used. It is also easier to automatically segment the second image data sets because the signal difference between the region of the lung and the surrounding tissue is greater since the region of the lung has only noise signals.

Figure 9:
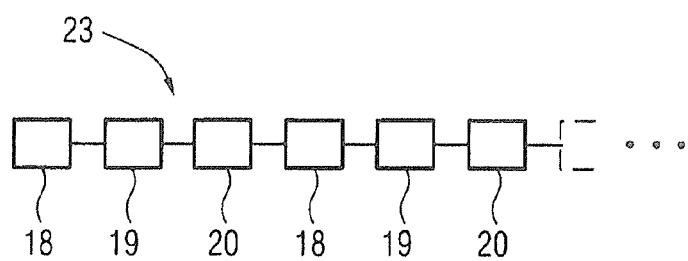
FIG. 9 shows a third embodiment of successive image recordings.

As shown in FIG. 9, in a further embodiment, it is possible to record additional data sets 20 with axial position. In such successive image recording 23, an image data set 18 with coronal position is followed by an image data set 19 with sagittal position, which is followed by an image data set 20 with axial position. Each image data set 18 with coronal position is a first image data set, and the image data sets 19 and 20 with sagittal and axial position can be designed as first or second image data sets. This possibility is available in all embodiments.

Figure 10:
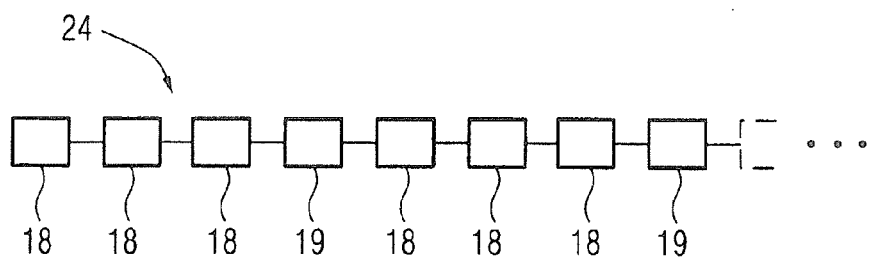
FIG. 10 shows a fourth embodiment of successive image recordings.

FIG. 10 shows successive image recordings which are also able to work with two-dimensional image data sets, but which varies from the previous embodiments. In the succession of image recordings 24, several image data sets 18 with coronal position are recorded successively. This is followed by a single image data set 19 with sagittal position. It is possible to record two, three or four image data sets 18 with coronal position before an image data set 19 with sagittal position is recorded. Alternatively, it is also possible, after recording two, three or four image data sets 18 with coronal position, to record an image data set 19 with sagittal position and an image data set 20 with axial position. This pattern can be repeated as many times as required. The density change of the lung tissue is determined by means of the image data sets 18 with coronal position. In addition, the image data sets 19 and 20 with sagittal and axial position are used to determine the volume change. FIG. 9 describes how they are arranged as first and/or second image data sets.

Figure 11:
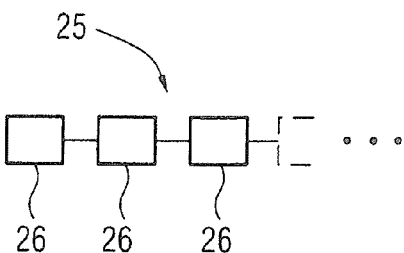
FIG. 11 shows a fifth embodiment of successive image recordings.

FIG. 11 shows a variation in the succession of image recording 21. In the context of the succession of image recording 25, image data sets with coronal position and navigator echoes 26 are recorded repeatedly. These navigators, or navigator echoes, can track a single point, or even different points, of the tissue surrounding the lung in order to acquire information about the change of lung volume. Naturally, the image data sets with navigator echoes 26 are first image data sets. Since the person 5 is lying on the patient bed 4, it is especially practical to track a point in the front area of the person 5. When a person is in lying position, there is little potential for the lung to expand in the region of the back, making it not very worthwhile to observe respective points in the back. In a data collection according to successive image recording 25, the lung volume is acquired in that an envelope curve of the lung is acquired from the image data sets 26 with coronal position, and a point outside the lung tissue in the front area of the person and certainly in the region of the lung is pursued by means of the navigator echo. Alternatively, the recording of the navigator echo also allows for a determination of projections, which makes it possible to track directly even an expansion of the lung volume.

It is certainly also possible to perform the successions of image recording 21 to 24 using image data sets with coronal position and navigator echo 26 instead of using simple image data sets 18 with coronal position.

In the same way, it is also possible to provide the image data sets 19 and 20 with sagittal and axial position with navigator echoes in all successions of image recording mentioned. This is independent of whether the image data sets 19 and 20 have been designed as first or second image data sets.

Figure 12:
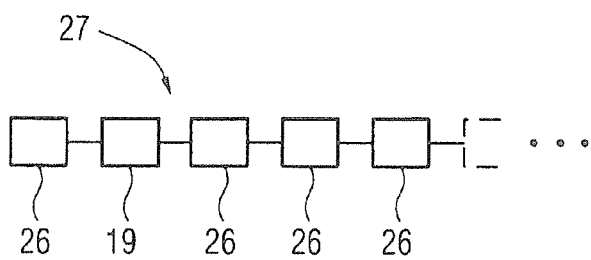
FIG. 12 shows a sixth embodiment of successive image recordings.

FIG. 12 shows a variation of the succession of image recording 25, in which after the first image data set with coronal position and navigator echo 26 an image data set 19 with sagittal position is recorded. The cross section of this image data set supplies the same information as the navigator echo which, in this case, comprises a projection. As a result, it is possible to compare the projection of the navigator echo with the spatial distribution of the respective tissue. It is then possible to use this information in calculating the volume change by means of the projections from the further navigator echoes.

Depending on the design of the measuring system used for recording the two-dimensional image data sets, it is also possible to record in multislice operation the image data sets 18 and/or 19 and/or 20 and/or 26 according to the successions of image recording 21 to 25 and 27 to 28. Using the RARE method involves, for example, a waiting period between recording the k-space line groups. As shown in FIG. 6, this waiting period is sufficient for recording, for example, several image data sets 18 with coronal position. For example, the number of layers can vary between two and ten. In this case, it is not necessary to record image data sets with sagittal or axial position.

Figure 13:
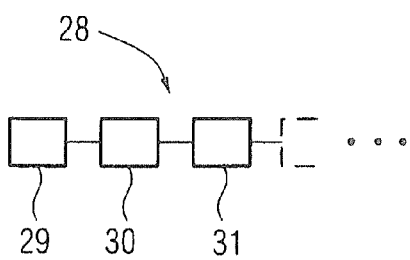
FIG. 13 shows a seventh embodiment of successive image recordings.

FIG. 13 shows successive image recording which is based on the successive image recordings described above. Here a first 3D image data set with maximum inspiration 29 is recorded and subsequently a second 3D image data set 30 with maximum expiration. It is also possible to reverse the temporal sequence of the 3D image data sets 29 and 30. Depending on the resolution of the 3D image data sets 29 and 30, each data recording requires between one and several seconds. Therefore, the person 5 has to hold his/her breath for recording the 3D image data sets 29 and 30 in order to avoid motion artifacts in the 3D image data sets. Apart from the motion artifacts, which could still be removed with additional data recording and post-processing procedures, it is also required to hold one's breath in order to maintain the lung volume at a constant level during the period of data recording. Maximum inspiration or expiration can involve the maximum value while breathing at rest. However, it can also represent the respective lung volume in maximum inspiration position or maximum expiration position. The 3D image data set 29 and 30 recordings are followed by successive image recordings 31. Each of the successive image recordings 21 to 25 and 27 to 28 can be used as a successive image recording 31. The volume change that can be determined from the image data sets 29 and 30 can, first of all, only be used for image data sets that also were recorded during respective periods of inspiration and expiration. For example, with the use of successive image recording 21, a differentiation between image data sets 18 with coronal position can be made only if one of the image data sets 18 with coronal position was recorded during maximum inspiration and the other one during maximum expiration. For the remaining differentiations the change in lung volume has to be interpolated. In the process, it is assumed, for example, that the lung volume changes consistently in the same time periods. However, there are other interpolation possibilities which take into consideration, for example, the breathing phase in which an image data set was recorded.

These successive image recordings can be simplified by recording only a 3D image data set 29 or 30. From this data set, the lung is segmented in three-dimensional fashion in order to acquire a 3D model of the enveloping surfaces of the lung. From the subsequent two-dimensional image data sets, the respective envelope curves of the lung are determined and the 3D model is adapted to this lung profile. In this way, the volume of the lung can be acquired at each point in time at which a two-dimensional image data set is available. As a final result, a three-dimensional model can be acquired for the time period.

It is certainly possible to record the 3D image data set 29 or 30 at any other point in time than the beginning of successive image recording. This generalization applies to all embodiments described. For the preparation of the 3D model of the enveloping surfaces of the lung it is not important at what point during the measurement the data was acquired. However, recording the 3D image data set 29 and/or 30 at the beginning of the examination has the advantage that, because the 3D model of the enveloping surfaces of the lung is available at the beginning of recording the two-dimensional image data sets and subsequent calculation of the quantitative ventilation changes, it is possible to represent them in real time. Otherwise, this representation can be performed only after the three-dimensional image data set has been recorded.

With regard to the representation, it is preferred to use a false-color display. In the process, one color, which is taken from a suitable color scale, represents the change of air content in the respective voxel.

Figure 14:
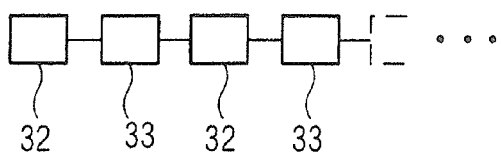
FIG. 14 shows an eighth embodiment of successive image recordings.
Figure 15:
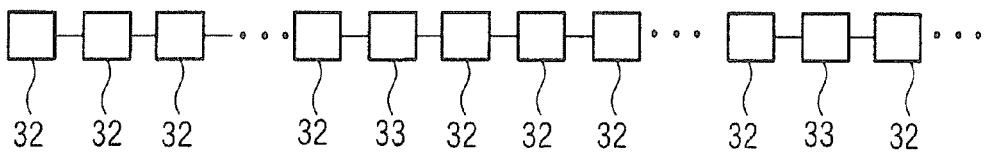
FIG. 15 shows a ninth embodiment of successive image recordings.

The successive image recordings described can be represented in an even more generalized fashion. FIG. 13 shows a successive image recording in which a dense image data set 32 and a volume image data set are recorded alternately in succession. By determining a differential image of two dense image data sets 32, it is possible to acquire information regarding the density change of the lung tissue, while the difference of two volume image data sets 33 describes a volume change. As described above and shown in FIG. 14, it is also possible to use other successions in which several dense image data sets 32 are followed by a volume image data set 33. The dense image data sets 32 are designed as first image data sets. The volume image data sets 33 are designed as first and second image data sets. This applies to all embodiments.

In a further embodiment, the image data sets 29 and 30 can be recorded as two-dimensional image data sets in multislice operation. In the process, it is possible to arrange the layers in coronal, sagittal and even axial fashion. For recording such an image data set, it is, of course, necessary to select one of the three spatial arrangements.

In an ideal case, merely a succession of three-dimensional first image data sets is recorded, which are designed as first image data sets. If it is possible to record such a 3D image data set during the period of 200 ms, no further information is required. From the respective differences of such three-dimensional image data sets, it is possible to determine the density changes of the lung tissue as well as the volume changes of the lung, in order to determine from the results a localized and quantitative ventilation change.

In a further embodiment, the volume or the volume flow of the inhaled and exhaled air is determined in addition to the image data set recordings. For this purpose, the person breaches into a spirometer which is, of course, designed MR compatible. The use of the spirometer provides additional information about the respiratory flow and the volume change of the lung as a whole. This information provides the possibility to determine the breathing loop even without using whole-body plethysmography. In addition, the invention-based method allows for a determination of the residual volume, which cannot be recorded by means of spirometry.

Although modifications and changes may be suggested by those skilled in the art, it is the intention of the inventor to embody within the patent warranted hereon all changes and modifications as reasonably and properly come within the scope of his contribution to the art.

We claim:

1. For a subject respirating in successive respiratory cycles, each comprising inspiration comprising mechanical intake of fresh gas and expiration comprising mechanical expulsion of breathed gas, a method for generating a quantitative indicator of ventilation that indicates a relation between said intake and said expulsion, said method comprising:

operating a magnetic resonance (MR) data acquisition unit to acquire at least two lung-representing first MR image data sets from the subject, with one of said first MR data sets being acquired in an inspiratory phase of said respiratory cycles and another of said first MR data being acquired in expiratory phase of said respiratory cycles, each of said first MR image data sets comprising pixels having respective intensity values produced by MR signals originating from lung tissue in a lung of the subject;

in a processor, automatically determining a difference in respective intensities between pixels in a region in said one of said first MR image data sets and pixels in a same region in said another of said first MR image data sets, said difference representing a density change of said lung tissue in said region due to said respirating;

in said processor, also automatically determining a volume, selected from the group consisting of a volume of a lung of the subject and a volume of the thorax of the subject, from two of said first MR image data sets or from at least one second image data set acquired from the subject; and in said processor, automatically calculating a quantitative indicator of ventilation for said region, that is spatially-resolved by the pixels in said region, as a predetermined mathematical relationship of said density change of said lung tissue in said region and said volume of a lung, and making said spatially-resolved quantitative indicator of ventilation available as an output from said processor in a humanly-perceptible form.

2. A method according to claim 1, comprising operating said magnetic resonance data acquisition unit to acquire at least one of the first image data sets in three spatial dimensions.

3. A method according to claim 1, comprising operating said magnetic resonance data acquisition unit to acquire at least one of the first image data sets in two spatial dimensions.

4. A method according to claim 3, comprising operating said magnetic resonance data acquisition unit to acquire at least two of the first image data sets with said two spatial dimensions and in multislice operation.

5. A method according to claim 1, comprising operating said magnetic resonance data acquisition unit to acquire at least a second image data set representing the lung in three spatial dimensions.

6. A method according to claim 5, comprising generating a 3D model of an outline of a lung from the second image data set, and determining said volume from said outline.

7. A method according to claim 1, comprising operating said magnetic resonance data acquisition unit to acquire said at least one second image data set in two spatial dimensions.

8. A method according to claim 7, comprising acquiring at least two of said second image data sets substantially orthogonally relative to each other, and determining said volume from said two image data sets.

9. A method according to claim 1 wherein said second image data set comprises image signals each having a signal intensity, and comprising segmenting a region from the image signals of the second image data set using a threshold value of the signal intensity, and determining said volume from the segmented region.

10. A method according to claim 1, comprising operating said magnetic resonance data acquisition unit to acquire at least one additional navigator echo for at least two of the first image data sets, and using said navigator echo to determine said volume.

11. A method according to claim 10, comprising determining said volume from elasticity values of selected tissue and acquiring said navigator echo as an MR echo signal that tracks respective points of a said selected tissue.

12. A method according to claim 1, comprising operating said magnetic resonance data acquisition unit to acquire at least one of said first image data sets with maximum respiratory inspiration, and to acquire at least one other of said first image data sets with maximum respiratory expiration.

13. A method according to claim 1, further comprising recording said respirator cycles with a respiratory sensor.

14. A method according to claim 13, comprising employing a spirometer as the respiratory sensor.

15. A method according to claim 1, comprising determining said quantitative indicator of ventilation using a calibration curve that describes said relation between the density change and the volume.

* * * * *